US012083448B2

(12) United States Patent
Jones et al.

(10) Patent No.: US 12,083,448 B2
(45) Date of Patent: Sep. 10, 2024

(54) PURIFICATION AND LABELING OF EXTRACELLULAR VESICLES USING A MIXED MODE RESIN COMPOSITION

(71) Applicant: The United States of America, as represented by the Secretary, Department of Health and Human Services, Bethesda, MD (US)

(72) Inventors: Jennifer C. Jones, Bethesda, MD (US); Joshua A. Welsh, North Bethesda, MD (US); Katherine M. McKinnon, Germantown, MD (US); Jay A. Berzofsky, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 891 days.

(21) Appl. No.: 16/959,071

(22) PCT Filed: Dec. 28, 2018

(86) PCT No.: PCT/US2018/067913
§ 371 (c)(1),
(2) Date: Jun. 29, 2020

(87) PCT Pub. No.: WO2019/133842
PCT Pub. Date: Jul. 4, 2019

(65) Prior Publication Data
US 2020/0330899 A1    Oct. 22, 2020

Related U.S. Application Data

(60) Provisional application No. 62/612,040, filed on Dec. 29, 2017.

(51) Int. Cl.
*B01D 15/34* (2006.01)
*B01D 15/38* (2006.01)
*G01N 33/545* (2006.01)

(52) U.S. Cl.
CPC ......... *B01D 15/34* (2013.01); *B01D 15/3804* (2013.01); *B01D 15/3847* (2013.01); *G01N 33/545* (2013.01)

(58) Field of Classification Search
CPC ............... B01D 15/34; B01D 15/3804; B01D 15/3847; G01N 33/545
See application file for complete search history.

(56) References Cited

FOREIGN PATENT DOCUMENTS

EP    2711712 A1    3/2014
EP    3228709 A1    10/2017
(Continued)

OTHER PUBLICATIONS

Cytiva, "Capto Core 700 multimodal chromatography resin".*
(Continued)

*Primary Examiner* — Benjamin L Lebron
(74) *Attorney, Agent, or Firm* — Leydig, Voit & Mayer, Ltd.

(57) ABSTRACT

Disclosed is a method of purifying extracellular vesicles in a sample comprising extracellular vesicles and molecules that are not bound to the extracellular vesicles. The method includes (a) providing a mixed mode resin composition containing a first resin having pores with a pore size that traps unbound molecules by at least by a size exclusion mechanism, and a second resin containing at least one affinity ligand; (b) contacting the sample with the mixed mode resin composition to trap at least a portion of the unbound molecules; and (c) separating the sample from the mixed mode resin composition and obtaining a sample containing extracellular vesicles at a higher concentration (Continued)

than prior to step (b). Further disclosed is a method of labeling an extracellular vesicle with a fluorophore that labels proteins which includes the use of a mixed mode resin composition.

14 Claims, 8 Drawing Sheets

(56) References Cited

FOREIGN PATENT DOCUMENTS

| WO | WO 2012/006476 A2 | 1/2012 |
|---|---|---|
| WO | WO 2013/124474 A2 | 8/2013 |
| WO | WO 2015/048566 A1 | 4/2015 |
| WO | WO 2016/162308 A1 | 10/2016 |
| WO | WO 2016/201064 A1 | 12/2016 |
| WO | WO 2017/083286 A1 | 5/2017 |

OTHER PUBLICATIONS

Lagoutte, P., et al., "Scalable chromatography-based purification of virus-like particle carrier for epitope based influenza A vaccine produced in *Escherichia coli*", Journal of Virological Methods, 232, pp. 8-11. (Year: 2016).*
GE Healthcare Bio-sciences AB, "HiTrap Heparin HP". (Year: 2014).*
Balaj et al., "Heparin Affinity Purification of Extracellular Vesicles," *Scientific Reports*, 5:10266, 1-15 (2015).
Böing et al., "Single-step Isolation of Extracellular Vesicles by Size-exclusion Chromatography," *Journal of Extracellular Vesicles*, 3(1): 23430, 11 pages (2014).
Brett et al., "Immunoaffinity Based Methods are Superior to Kits for Purification of Prostate Derived Extracellular Vesicles from Plasma Samples," *The Prostate*, 77:1335-1343 (2017).
Corso et al., "Reproducible and Scalable Purification of Extracellular Vesicles Using Combined Bind-elute and Size Exclusion Chromatography," Scientific Reports, 7:11561, 1-15 (2017).
Davies et al., "Microfluidic Filtration System to Isolate Extracellular Vesicles From Blood," *Lab Chip*, 12(24): 5202-5210 (2012).
Dorman, "Noncoding RNA Tool Enhances Translation," BioTechniques 59(1):7 (Jul. 2015).
Echevarria et al., "Microarray-based Identification of Lectins for the Purification of Human Urinary Extracellular Vesicles Directly from Urine Samples," *ChemBioChem*, 15: 1621-1626 (2014).
European Patent Office, International Search Report mailed Mar. 18, 2019, PCT/US2018/067913.
European Patent Office, Written Opinion of the International Searching Authority mailed Mar. 18, 2019, PCT/US2018/067913.
James et al., "Novel High-throughput Approach for Purification of Infectious Virions," *Scientific Reports*, 6: 36826, 1-12 (2016).
Lee et al., "Cellular Engineering with Membrane Fusogenic Liposomes to Produce Functionalized Extracellular Vesicles," *ACS Appl. Mater. Interfaces*, 8: 6790-6795 (2016).
Li et al., "Progress in Exosome Isolation Techniques," Theranostics, 7(3): 789-804 (2017).
Morales-Kastresana et al., "Labeling Extracellular Vesicles for Nanoscale Flow Cytometry," *Scientific Reports*, 7: 1878-1887(2017).
Mørk et al., "Prospects and Limitations of Antibody-mediated Clearing of Lipoproteins from Blood Plasma Prior to Nanoparticle Tracking Analysis of Extracellular Vesicles," Journal of Extracellular Vesicles, 6: 1-10 (2017).
Nakai et al., "A novel Affinity-based Method for the Isolation of Highly Purified Extracellular Vesicles," *Scientific Reports*, 6: 33935, 1-12 (2016).
Pocsfalvi et al., "Chromatography and its Hyphenation to Mass Spectrometry for Extracellular Vesicle Analysis," Journal of Chromatography, 1439: 26-41 (2016).
Pospichalova et al., "Simplified Protocol for Flow Cytometry Analysis of Fluorescently Labeled Exosomes and Microvesicles using Dedicated Flow Cytometer," Journal of Extracellular Vesicles, 4:25530, 1-15 (2015).
Welton et al., "Ready-made Chromatography Columns for Extracellular Vesicle Isolation from Plasma," *Journal of Extracellular Vesicles*, 4: 1-9 (2015).
Xu et al., "Quantification of Small Extracellular Vesicles by Size Exclusion Chromatography with Fluorescence Detection," *Anal. Chem.*, 88(21): 10390-10394 (2016).
Zhang et al., "Mixed-mode Chromatography in Pharmaceutical and Biopharmaceutical Applications," *Journal of Pharmaceutical and Biomedical Analysis*, 128: 73-88 (2016).

* cited by examiner

PURIFICATION AND LABELING OF EXTRACELLULAR VESICLES USING A MIXED MODE RESIN COMPOSITION

CROSS-REFERENCE TO RELATED APPLICATIONS

This patent application is a U.S. National Phase Patent Application of co-pending International Patent Application No. PCT/US2018/067913, filed Dec. 28, 2018, which claims the benefit of U.S. Provisional Patent Application No. 62/612,040, filed Dec. 29, 2017, both of which are incorporated by reference in their entireties herein for all purposes.

STATEMENT REGARDING FEDERALLY SPONSORED RESEARCH AND DEVELOPMENT

This invention was made with Government support under project number ZIA BC011502 awarded by the National Institutes of Health, National Cancer Institute. The Government has certain rights in this invention.

BACKGROUND OF THE INVENTION

Extracellular vesicles (EVs) include exosomes that are about 30-100 nm in size and greater than about 700 kDa. EVs are released by cells and carry protein and nucleic acid (e.g., mRNA) cargo within a surface membrane structure. Due to the nature and biological activity of components of the cargo carried by EVs, there is great interest in using EVs as biomarkers or as vehicles for targeted delivery of therapeutic molecules. As a matter of practicality, however, the small size of EVs preclude the use of standard purification methods (e.g., centrifugation) that are commonly used for cells and platelets, which are much larger in comparison at >5,000 nm and >1,000 nm, respectively.

A size exclusion chromatographic method for separating EVs from the majority of plasma or serum proteins, which are abundant in biofluid preparations, has been reported using a SEPHAROSE™ resin (GE Healthcare, Chicago, IL). See, for example, Böing et al., *Journal of Extracellular Vesicles*, 3(1): 23430 (2014). While this method reportedly is effective in removing some proteins from a sample containing EVs, residual proteins and other undesirable molecules tend to remain. Moreover, the size exclusion chromatographic method is limited in that each sample must be processed individually. Other known EV purification methods are not broadly applicable for biofluid processing, are not scalable for high-throughput (HTS) processing (e.g., compatible with robotic 96- or 384-well formats), and/or are not applicable for good manufacturing practice (GMP) large scale production, which is necessary for therapeutic exosome-based therapeutics.

In view of the foregoing, there remains an unmet need to provide novel methods that effectively purify extracellular vesicles and that are suitable for robotic, high-throughput systems.

BRIEF SUMMARY OF THE INVENTION

The invention provides a method of purifying EVs in a sample comprising EVs and molecules that are not bound to the EVs. Specifically, the method comprises: (a) providing a mixed mode resin composition comprising a first resin having pores with a pore size that traps unbound molecules having a size less than or equal to 1,000,000 Da in its pores by at least by a size exclusion mechanism, and a second resin comprising at least one affinity ligand; (b) contacting the sample with the mixed mode resin composition for a time sufficient to trap at least a portion of the unbound molecules having a size less than or equal to 1,000,000 Da in the first resin from the sample; and (c) separating the sample from the mixed mode resin composition after the contacting in (b) and obtaining a sample containing EVs at a higher concentration than prior to step (b).

Further provided is a method of labeling an EV comprising (a) contacting an EV and a fluorophore that labels proteins to provide a mixture comprising a labeled EV and unbound fluorophore; (b) removing the unbound fluorophore by contacting the mixture with a mixed mode resin composition comprising a first resin and a second resin, wherein the first resin removes the unbound fluorophore and any other unbound molecules by a size exclusion mechanism; and the second resin transiently and reversibly binds to the labeled EV in a calcium-dependent manner; (c) first eluting any unbound molecules; and (d) second eluting in the presence of at least one additive that selectively elutes the EV. Removing residual unbound fluorophore and other unbound molecules results in a sample containing fluorolabeled EVs with increased detection sensitivity (e.g., an increased signal to noise ratio) for use in, e.g., proteomic analysis, cytometric studies, or nanoparticle analysis.

BRIEF DESCRIPTION OF THE SEVERAL VIEWS OF THE DRAWING(S)

FIG. 1 is a schematic illustration of a method of purifying EVs using a mixed mode resin composition in accordance with an embodiment of the invention. EVs obtained from blood plasma or tissue culture are centrifuged to obtain EV-enriched samples. The samples are added to an incubation tube and a mixed mode resin composition is added. After incubating, the EVs are eluted.

FIG. 2A is a schematic illustration of a sample comprising EVs (○) and unbound molecules (Δ) that is contacted with a mixed mode resin composition, in which the second resin has an affinity for large unbound molecules. FIG. 2B is a schematic illustration of a sample comprising EVs (○) and unbound molecules (Δ) that is contacted with a mixed mode resin composition, in which the second resin has an affinity for EVs.

FIG. 3 is a gel electrophoresis pattern of unstained and CFSE-stained PC3pip EVs.

FIG. 4 is graph of time (before incubation, after 30 min incubation, and after 30 min+ an additional 30 min incubation) versus amount of bovine serum albumin (μg) in a sample.

DETAILED DESCRIPTION OF THE INVENTION

Figure 1:
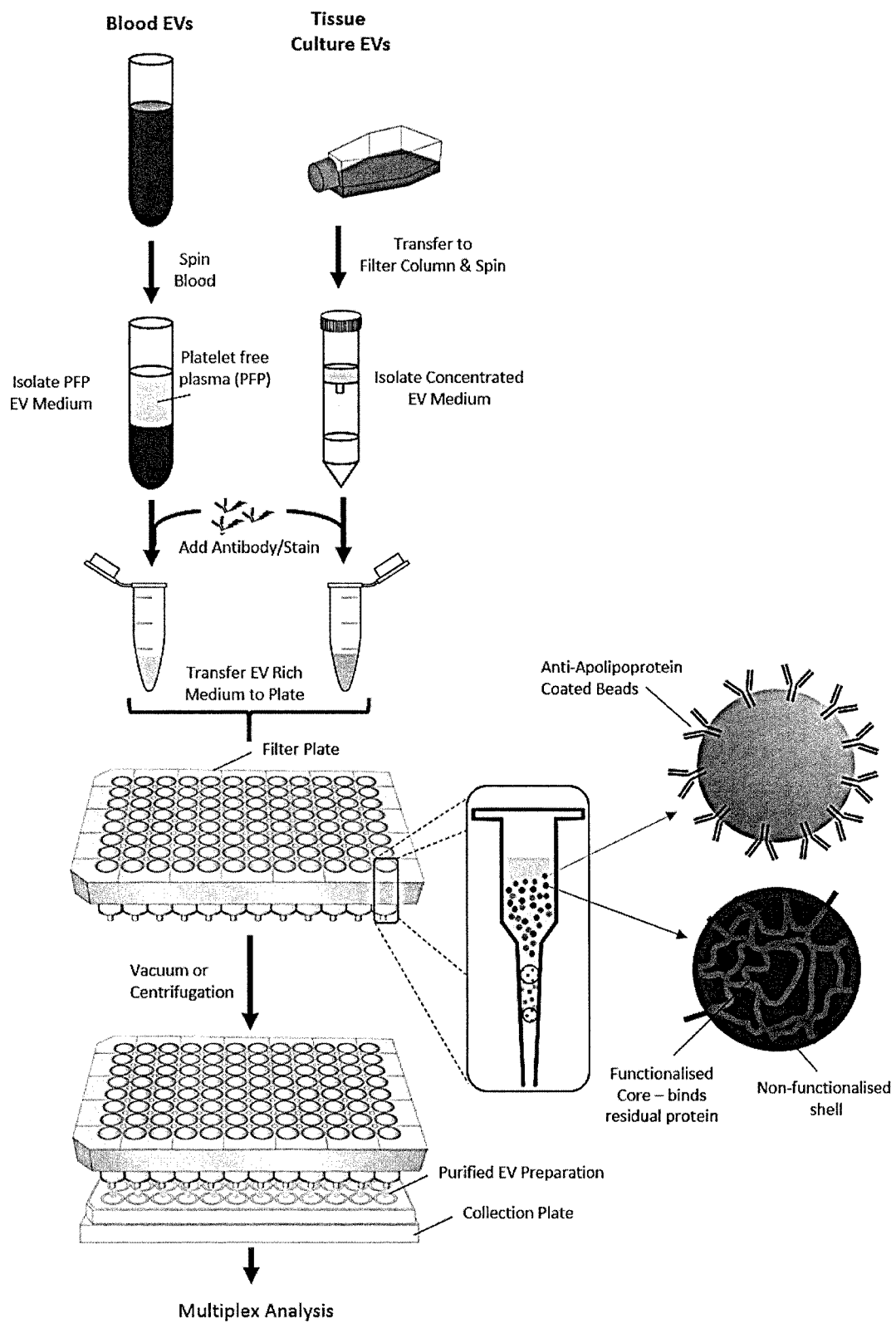

The inventive methods have an advantage over existing purification methods because known methods generally purify EVs by density, size, or positive selection. The methods described herein purify the EVs by either (i) size and negative selection or (ii) size and transient (i.e., reversible) positive selection.

In particular, the invention is directed to methods of purifying EVs in a sample comprising the use of a mixed mode resin composition of two different types of resins. One resin removes small unbound molecules (e.g., proteins and other labels) that are present in the sample and that have a molecular weight less than or equal to 1000 kDa. The first resin can be modified with respect to pore size to change the molecular weight cut off for entry into the resin (e.g., less than or equal to 900 kDa, less than or equal to 800 kDa, less than or equal to 700 kDa, less than or equal to 600 kDa, less than or equal to 500 kDa). The second type of resin has an affinity that is tunable for either larger unbound molecules (e.g., proteins and labels) or the EVs themselves, depending on the desired mode of separation. The methods described herein using the mixed mode resin composition provide at least one benefit, such as it is simple to use, fast, does not dilute the EV concentration, provides EVs with a high purity, increased yield relative to other known purification methods (e.g., polyethylene glycol-based precipitation, such as EXOQUICK™, and immunoaffinity only pulldown methods), high-throughput processing of samples, the ability to use preparative scale up production, and/or the ability to use small volumes of sample (e.g., µL sized).

Accordingly, the invention provides a method of purifying EVs in a sample comprising EVs and molecules that are not bound to the EVs. The method comprises:
  (a) providing a mixed mode resin composition comprising a first resin having pores with a pore size that traps unbound molecules having a size less than or equal to 1,000,000 Da in its pores by at least by a size exclusion mechanism, and
  a second resin comprising at least one affinity ligand;
  (b) contacting the sample with the mixed mode resin composition for a time sufficient to trap at least a portion of the unbound molecules having a size less than or equal to 1,000,000 Da in the first resin from the sample; and
  (c) separating (e.g., isolating) the sample from the mixed mode resin composition after the contacting in (b).

After step (b), the sample contains EVs at a higher concentration than prior to step (b). In other words, contrary to methods that rely solely on a size exclusion mechanism, the present method does not dilute the concentration of EVs in the sample. Moreover, unlike methods that rely solely on an immunoaffinity mechanism, the present method does not add unnecessary labels or ligands, as the eluted EVs are obtained in their native form.

The sample used in the present method comprises EVs and unbound molecules. If desired, prior to the start of the method, the sample can be filtered and/or centrifuged to remove some unbound molecules, however, such step is not required. In some embodiments, the sample is not filtered or centrifuged to remove unbound molecules (e.g., protein, labels, etc.) prior to step (a) of any of the methods described herein.

The sample can be from any suitable source, such as a biofluid or a cell culture supernatant. In some embodiments, the sample is from a biofluid (e.g., plasma, serum, urine, cerebrospinal fluid, saliva, tears, ascites, and pleural effusion), tissue culture supernatants (e.g., tissue from any organ, such as kidney, liver, heart, lung, prostate, skin, stomach, bladder, bone, breast, ovary, pancreas, brain, intestine, or adrenals), or even purified EVs that have been conjugated to a protein (e.g., a monoclonal antibody) or other label (e.g., fluorescent dye).

FIG. 1 illustrates a method of purifying EVs using a mixed mode resin composition. EVs obtained from blood plasma or tissue culture are centrifuged to obtain EV-enriched samples. The samples are added to an incubation tube and a mixed mode resin composition is added. After incubating, the sample is eluted to isolate the sample in which EVs have a higher concentration than the start due to a portion of unbound molecules being removed from the sample.

The unbound molecules in the sample comprise at least one protein, polypeptide, peptide, lipoprotein (e.g., chylomicrons, very low density lipoprotein, intermediate density lipoprotein, low density lipoprotein, and high density lipoprotein), nucleic acid (e.g., deoxyribonucleic acid (DNA) and ribonucleic acid (RNA)), synthetic label (e.g., a fluorescent dye, radioactive isotope), metals or halogen (e.g., sodium, potassium, calcium, magnesium, iron, cobalt, molybdenum, chromium, copper, manganese, zinc, selenium, chlorine, and iodine), or a combination thereof. Proteins include those found in biofluids, e.g., blood, urine, cerebrospinal fluid, saliva, tears, and breast milk or organs such as, the gut, respiratory tract, urogenital tract, and mucosal tissue. For example, the protein can be an antibody (e.g., a monoclonal antibody or a polyclonal antibody), apolipoprotein A (ApoA), apolipoprotein B (ApoB), apolipoprotein E (ApoE), immunoglobulin G (IgG), immunoglobulin M (IgM), immunoglobulin A (IgA), immunoglobulin E (IgE), immunoglobulin D (IgD), albumin, globulin, factor IX, Tamm-Horsfall protein, transferrin, haptoglobin, prothrombin, alpha 1 acid glycoprotein, alpha 1 fetoprotein, cystatin C, ceruloplasmin, or any combination thereof.

In some embodiments, the nucleic acid (e.g., deoxyribonucleic acid (DNA) and ribonucleic acid (RNA)) is within the EVs. In this embodiment the nucleic acid can be up to 10 kilobases. In some embodiments, the nucleic acid is folded, thereby allowing it to fit within the EVs.

In some embodiments, the nucleic acid (e.g., deoxyribonucleic acid (DNA) and ribonucleic acid (RNA)) is not within the EVs and is desirable to separate it from the EVs. In this case, the nucleic acid may have a molecular weight less than or equal to 1000 kDa (e.g., less than or equal to 900 kDa, less than or equal to 800 kDa, less than or equal to 700 kDa, less than or equal to 600 kDa, less than or equal to 500 kDa) by at least a size exclusion mechanism, whereas the second resin has an affinity for either unbound molecules (e.g., unbound molecules with a molecular weight greater than 1000 kDa (e.g., greater than 900 kDa, greater than 800 kDa, greater than 700 kDa, greater than 600 kDa, or greater than 500 kDa)) or the EVs themselves.

In some embodiments, the nucleic acid (e.g., deoxyribonucleic acid (DNA) and ribonucleic acid (RNA)) is not within the EVs and is desirable to separate it from the EVs. In this case, the nucleic acid may be less than or equal to 30 kilobases (e.g., less than or equal to 29 kilobases, less than or equal to 28 kilobases, less than or equal to 27 kilobases, less than or equal to 26 kilobases, less than or equal to 25 kilobases, less than or equal to 24 kilobases, less than or equal to 23 kilobases, less than or equal to 22 kilobases, less than or equal to 21 kilobases, less than or equal to 20 kilobases, less than or equal to 19 kilobases, less than or equal to 18 kilobases, less than or equal to 17 kilobases, less than or equal to 16 kilobases, less than or equal to 15 kilobases, less than or equal to 14, kilobases less than or equal to 13, kilobases less than or equal to 12 kilobases, less than or equal to 11 kilobases, less than or equal to 10 kilobases, less than or equal to 9 kilobases, less than or equal to 8 kilobases, less than or equal to 7 kilobases, less than or equal to 6 kilobases, less than or equal to 5 kilobases, less than or equal to 4 kilobases, less than or equal to 3 kilobases, less than or equal to 2 kilobases, or less than or equal to 1 kilobase) by at least a size exclusion mechanism.

Step (a) is directed to providing a mixed mode resin composition comprising a first resin and a second resin, in which the two types of resins operate by different mechanisms that enable the removal of a wide range of unbound molecules. Specifically, the first resin removes unbound molecules having a molecular weight less than or equal to 1000 kDa (e.g., less than or equal to 900 kDa, less than or equal to 800 kDa, less than or equal to 700 kDa, less than or equal to 600 kDa, less than or equal to 500 kDa) by at least a size exclusion mechanism, whereas the second resin has an affinity for either unbound molecules (e.g., unbound molecules with a molecular weight greater than 1000 kDa (e.g., greater than 900 kDa, greater than 800 kDa, greater than 700 kDa, greater than 600 kDa, or greater than 500 kDa)) or the EVs themselves.

In embodiments of the method, the first resin in the mixed mode resin composition comprises a first bead comprising (i) a porous core comprising a matrix material and at least one affinity ligand and (ii) a porous shell. In this aspect of the invention, the core is considered functionalized in that the at least one affinity ligand can bind (i.e., trap) an unbound molecule (e.g., a protein) with a size that can pass through the porous shell. In general, the porous shell typically is non-functionalized, such that the porous shell does not contain any active groups. In some instances, however, the first bead can be functionalized to include at least one second affinity ligand, as described herein, that is coated on the exterior surface of the bead. Thus, the first resin can remove unbound molecules in the sample by size exclusion mechanism and an affinity mechanism (via the core and/or the exterior).

Figure 2A:
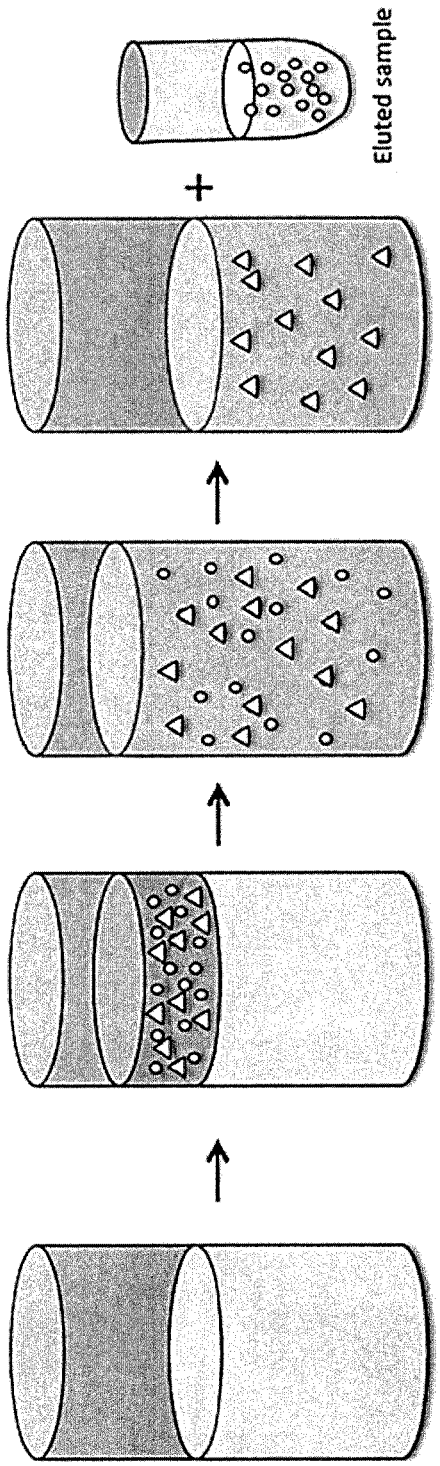

The second resin in the mixed mode resin composition comprises at least one affinity ligand. Depending on the nature of the affinity ligand, the second resin can bind to at least one unbound molecule present in the sample or the EVs. When binding an unbound molecule, the unbound molecule typically will have a molecular weight that is greater than the size cut off for the first resin, e.g., a molecular weight greater than 1000 kDa (e.g., greater than 900 kDa, greater than 800 kDa, greater than 700 kDa, greater than 600 kDa, or greater than 500 kDa). This method is illustrated in FIG. 2A, in which a sample comprising EVs and unbound molecules is contacted with a mixed mode resin composition. Unbound molecules are trapped by either the first resin or second resin. Unbound EVs are eluted and isolated from the mixed mode resin composition and unbound molecules.

When a positive selection of EV is desired, the second resin can have an affinity ligand that transiently binds to the EV in a calcium-dependent manner. For example, the ligand can have an affinity to bind to a phospholipid membrane in the EV and/or a heparin-binding molecule on the surface of the EV. In a preferred embodiment of this method, the ligand is a calcium-dependent phospholipid ligand that comprises a phosphatidylserine receptor, such as a transmembrane immunoglobulin and mucin domain (TIM) protein (e.g., a TIM-4 fusion protein) or annexin V, that can conjugate to a functional group on a protein (e.g., —NH$_2$, —COOH, or —SH group) that exists on the surface of the EV. In another preferred embodiment, the affinity ligand is heparin.

Figure 2B:
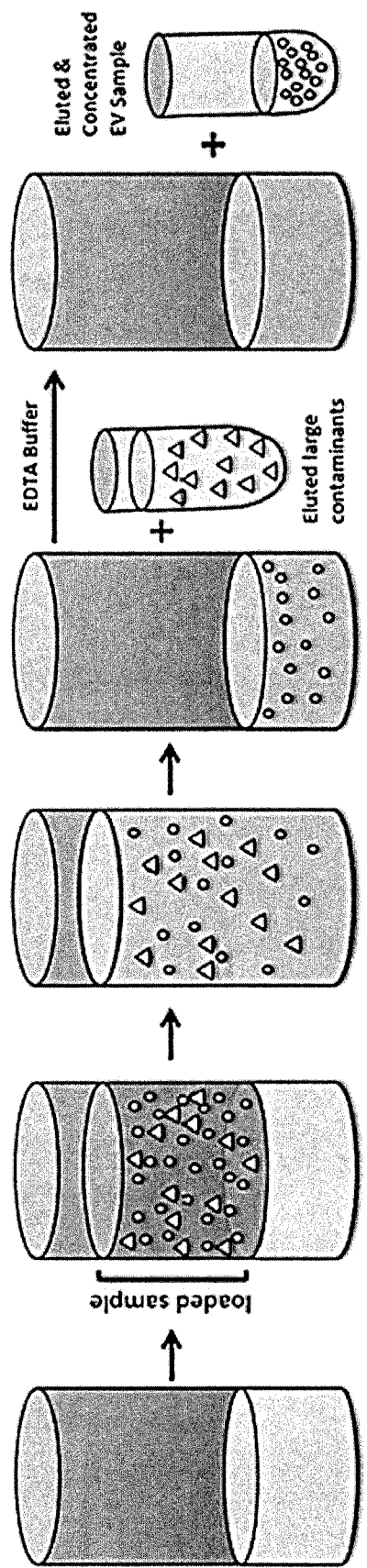

Typically, when a positive selection of EVs is desired, the method will include additional steps after step (b), including (b-2) first eluting, typically in the presence of calcium, any molecule not bound to the first and second resins; and (b-3) second eluting in the presence of at least one additive (e.g., chelating agent and/or salt), wherein the second eluting selectively elutes the EVs. This method is illustrated in FIG. 2B, in which a sample comprising EVs and unbound molecules is contacted with a mixed mode resin composition. Small sized unbound molecules get trapped by the first resin, whereas EVs are bound by the second resin. Large sized unbound molecules are eluted from the column. In the presence of an additive, such as a calcium chelator (e.g., EDTA buffer) and/or high salt solution, the bound EVs are unconjugated from the second resin and eluted from the column.

The first eluting step (b-2) may include an eluent that comprises a calcium ion and other optional additives. The source of the calcium ion is not particularly limited and includes for example, calcium chloride, calcium bromide, calcium iodide, calcium hydroxide, calcium hydrogen carbonate, calcium acetate, and mixtures thereof. The concentration of calcium is not particularly limited so long as there is sufficient calcium (e.g., about 1 mM) to enable the binding of the second resin to a phospholipid membrane on the EV. Optional additives include a buffer (e.g., phosphate buffer, a bicarbonate-carbonate buffer, citrate buffer, and/or one of Good's buffers), salts (sodium acetate, sodium chloride, sodium phosphate, potassium acetate, potassium chloride, and potassium phosphate), and surfactants (e.g., polysorbate 20, polysorbate 80, polyethylene glycol p-(1,1,3,3-tetramethylbutyl)-phenyl ether). Specific examples of suitable buffers include, e.g., phosphate-buffered saline (PBS), 4-(2-hydroxyethyl)-1-piperazineethanesulfonic acid (HEPES), 3-(N-morpholino)propanesulfonic acid (MOPS), piperazine-N,N'-bis(2-ethanesulfonic acid) (PIPES), and 2-(N-morpholino)ethanesulfonic acid (MES).

The second eluting step (b-3) may include an eluent that can contain one or more additives, as described herein. In some embodiments, the second eluting step takes place in the presence of at least one additive that selectively elutes the extracellular vesicle. Preferably the chelating agent that selectively elutes the purified extracellular vesicle is a chelating agent and/or salt.

For example, a chelating agent that is a calcium chelator can be used, which reduces the concentration of calcium in the mixture and, in turn, unconjugates the second resin from the EV. The calcium chelator can be, e.g., ethylenediaminetetraacetic acid (EDTA), ethylenediamine-N,N'-disuccinic acid (EDDS), ethylene glycol-bis(β-aminoethyl ether)-N,N,N',N'-tetraacetic acid (EGTA), Fura-2, (1,2-bis(o-aminophenoxy)ethane-N,N,N',N'-tetraacetic acid) (BAPTA), 5,5'-dibromo-BAPTA, 5,5'-difluoro-BAPTA, 5,5'-dimethyl-BAPTA, 5-methyl-5'-nitro-BAPTA, 5-nitro-BAPTA, 4-trifluoromethyl-BAPTA, ethylenediamine, diethylenetriamine, catechol, cryptand, dimethylglyoxime, glutamic acid, gluconic acid, or a combination thereof. Preferably, the chelating agent comprises EDTA.

Alternatively, a salt in the form of a high salt solution can be used as the additive that selectively elutes the extracellular vesicle. The salt can be any suitable compound formed by a cation of Group I (e.g., Li, Na, K, Rb, or Cs) or II (Be, Mg, Ca, Sr, or Ba) of the Periodic Table or other cations (e.g., ammonium) and an anion of Group VI (O or S) or VII (F, Cl, Br, or I), or other anions (e.g., hydroxide, carbonate, bicarbonate, chlorate, dichlorate, sulfate, phosphate, nitrate, and nitrite). For example, the salt can be sodium chloride or potassium chloride.

In embodiments, the second resin comprises a bead comprising a matrix material and the surface of the bead is coated with at least one affinity ligand.

The first bead (i.e., core plus shell) and second bead can have any suitable size, but typically will range from about 30 µm to about 500 µm. For example, the first and/or bead can be at least 30 µm (e.g., at least 40 µm, at least 50 µm, at least 60 µm, at least 80 µm, at least 100 µm, at least 125 µm, at least 150 µm, at least 200 µm, at least 250 µm, at least 300 µm, at least 350 µm, at least 400 µm, or at least 450 µm). The first and/or second bead will generally be 500 µm or less (e.g., 450 µm or less, 400 µm or less, 350 µm or less, 300 µm or less, 250 µm or less, 200 µm or less, 150 µm or less, 125 µm or less, 100 µm or less, 80 µm or less, 50 µm or less, or 40 µm or less). In a particular example, the total diameter of the first and/or second bead will range from 40-100 nm (e.g., about 75 µm, about 85 µm, about 90 µm, etc.). Any two of the foregoing endpoints can be used to define a close-ended range, or a single endpoint can be used to define an open-ended range.

As used herein the term "about" typically refers to ±0.5% of a value, ±1% of a value, or ±2% of a value.

The thickness of the shell of the first bead is not particularly limited, but will tend to be relatively thin to allow for a larger interior capacity. For instance, the shell thickness can range from about 1 µm (e.g., at least 1 µm, at least 2 µm, at least 3 µm, at least 5 µm, at least 6 µm, at least 8 µm, at least 10 µm, at least 11 µm, at least 12 µm, at least 15 µm) to about 20 µm thick (e.g., 18 µm or less, 15 µm or less, 12 µm or less, 11 µm or less, 10 µm or less, 8 µm or less, 6 µm or less, 5 µm or less, 3 µgm or less, or 2 µm or less). In certain embodiments, the shell will be about 5 µm. Any two of the foregoing endpoints can be used to define a close-ended range, or a single endpoint can be used to define an open-ended range.

The porosity of the shell of the first bead is such that an unbound molecule (e.g., protein or other label) with a molecular weight less than or equal to 1000 kDa (e.g., less than or equal to 900 kDa, less than or equal to 800 kDa, less than or equal to 700 kDa, less than or equal to 600 kDa, or less than or equal to 500 kDa) can pass through the shell to the core of the bead. Generally, the porosity of the shell will be greater than the porosity of the core.

The matrix material of the resin (e.g., first and/or second bead) and/or the porous shell of the first bead can be made of any suitable material and typically comprises a synthetic polymer and/or a natural polymer. Examples of suitable polymers for the matrix material and/or the porous shell include a polystyrene, a polyalkylene, a polyester, polydivinylbenzene, an acrylamide polymer, a polyacrylate, a vinyl ester polymer, a vinylamide polymer, silica, agarose, agarobiose, agar, cellulose, dextran, chitosan, konjac, carrageenan, gellan, alginate, or a combination thereof.

In a preferred embodiment, the matrix material of the first bead is a natural polymer. More preferably, the matrix material of the first bead comprises or consists of agarose (e.g., cross-linked agarose).

The porous shell of the first bead can be the same material or a different material from the matrix material. Preferably, the porous shell is the same material as the matrix material. Preferably, the porous shell comprises or consists of agarose (e.g., cross-linked agarose).

The matrix material of the second bead preferably is a synthetic polymer, such as polystyrene, polyethylene, polypropylene, polyester, polydivinylbenzene, polyacrylamide, poly(meth)acrylate, polyethyl acrylate, polymethyl methacrylate, poly(hydroxyethyl) methacrylate, polyvinyl ester, poly(N-vinylacetamide), or a combination thereof.

The affinity ligand that can be present in the core of the first bead is any suitable ligand that has an affinity for (e.g., binds to) molecules in the sample that has a molecular weight less than or equal to 1000 kDa (e.g., less than or equal to 900 kDa, less than or equal to 800 kDa, less than or equal to 700 kDa, less than or equal to 600 kDa, or less than or equal to 500 kDa). In some embodiments, the first ligand can be an amine and/or a quaternary ammonium compound, such as a trialkylamine and a tetraalkylammonium compound. In this context, the alkyl group will generally range from $C_6$-$C_{14}$ (e.g., $C_6$, $C_8$, $C_{10}$, $C_{12}$, and/or $C_{14}$). The first ligand can be, for example, trihexylamine, trioctylamine, tridecylamine, tridodecylamine, tri-octyl/decyl amine, N-dodecenyl-trialkylmethylamine, N-benzyl-N-methyl ethanolamine, trilauryl monomethyl ammonium salt, N-methyl-N,N,N-trioctylammonium chloride, or a combination thereof. Preferably, the first ligand is trioctylamine.

The affinity ligand that is present on the second resin (e.g., second bead) and optionally present on the surface of the first bead is any suitable ligand that has an affinity for (e.g., binds to) molecules in the sample that have a molecular weight greater than 1000 kDa (e.g., greater than 900 kDa, greater than 800 kDa, greater than 700 kDa, greater than 600 kDa, or greater than 500 kDa). The affinity between the ligand and the large unbound molecules can be through hydrogen bonding, ionic bonding, covalent bonding, or a hydrophobic interaction. The affinity ligand can be an immunoglobulin and/or a biotinylated compound. For example, the second ligand can be an antibody, an antigen, streptavidin, biotin, avidin biotin, heparin, glutathione, protein A, protein G, protein A/G, an amino acid, a nucleotide, a carbohydrate, a lectin (e.g., concanavalin A), a dye, a chelate, or a combination thereof.

Step (b) is directed to contacting the sample with the mixed mode resin composition for a time sufficient to remove at least some of the unbound molecules from the sample. The contacting step takes place in any suitable container, such as a chromatography column, chromatography plate, tube, filter plate, glass slide (e.g., microscope slide or coverslip), or paper.

Figure 6A:
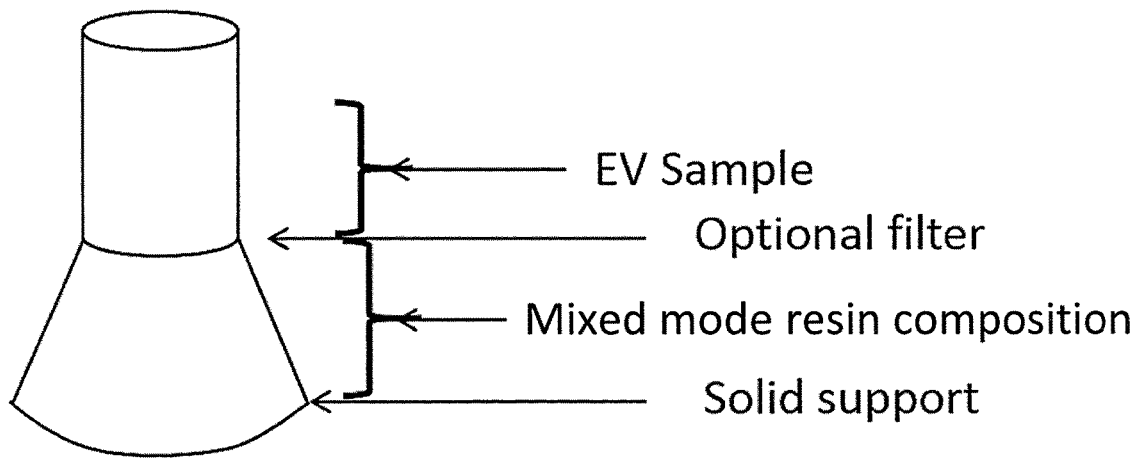
FIG. 6A is a schematic drawing showing a suitable container in which the contacting step of an embodiment of the invention can take place.

The suitable container can also be a tube with a top, bottom, and middle diameter, wherein the middle diameter is less than the bottom diameter (i.e., a flask beaker shape). The middle diameter of the "flask tube" refers to a position between the top and bottom diameter of the flask tube. The bottom of the flask tube should be closed and the top of the flask tube should be open. The reduced center diameter of the flask tube as compared the bottom diameter of the flask tube allows for an area within the flask tube with a reduced surface area between two liquids (as compared to a traditional straight sided Eppendorf tube with a taped bottom). See, for example, FIG. 6A. An optional filter can also be used near the middle diameter of the flask tube. The desired flask tube can be produced, for example, by a 3D printer. The flask tube can have a solid support at the bottom of the flask tube if desired. The flask tube should hold a volume of liquid between the center diameter and bottom diameter of the flask tube that is greater than the volume of liquid that can be held between the center diameter and the top diameter of the flask tube. The flask tube can have the sample in a location above the center diameter of the flask tube and the mixed mode resin composition below the center diameter of the flask tube. This configuration allows for less contamination when the liquids are separated by, for example, pipetting.

Figure 6B:
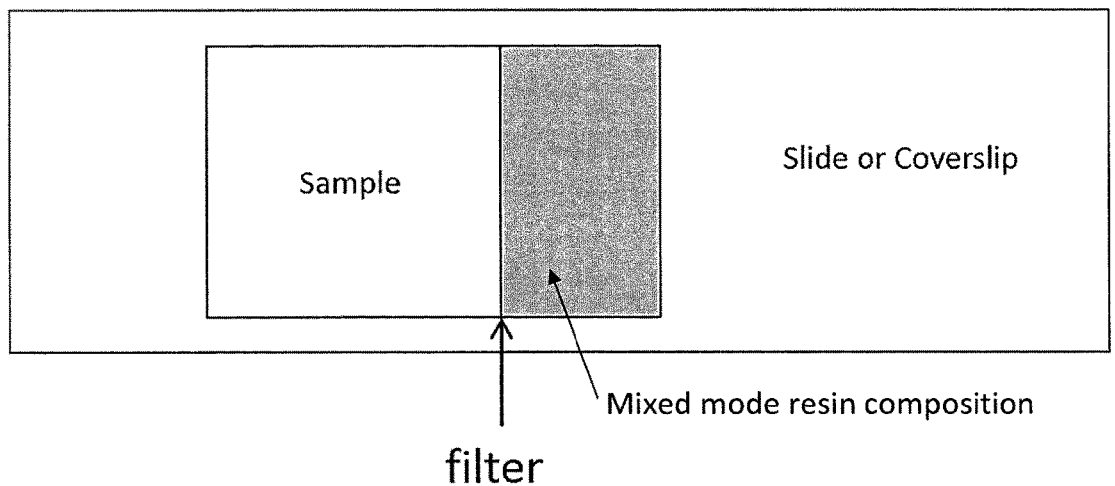
FIG. 6B is a schematic drawing showing another suitable container in which the contacting step of an embodiment of the invention can take place.

The suitable container can also be a cytometric chamber, such as a confocal or other microscopy imaging chamber. The glass slide can have the sample in a location next to the mixed mode resin composition. See FIG. 6B. An optional filter can also be used between the sample and the mixed mode resin composition. Unbound label diffuses through the filter and is sequestered by the mixed mode resin, thereby reducing levels of unbound label and background and improves assay sensitivity.

The contact time will vary depending on the composition of the sample. Typical contact (e.g., incubation) time will be 6 hours or less (e.g., 5 hours or less, 4 hours or less, 3.5 hours or less, 3 hours or less, 2.5 hours or less, 2 hours or less, 1.5 hours or less, 1 hour or less, or 45 minutes or less). In general, the contact (e.g., incubation) time will be 5 minutes or more (e.g., 10 minutes or more, 15 minutes or more, 20 minutes or more, 25 minutes or more, 30 minutes or more, 45 minutes or more, 60 minutes or more). Any two of the foregoing endpoints can be used to define a close-ended range or a single endpoint can be used to define an open-ended range. For example, preferably the sample is in contact with the mixed mode resin composition for about 0.5-4 hours.

The temperature of the contacting step is not particularly limited and can range from about 0° C. (e.g., about 2° C., about 4° C., about 10° C., or about 20° C.) to about 40° C. (e.g., about room temperature, about 10° C., about 20° C., about 25° C., or about 30° C.). Any two of the foregoing endpoints can be used to define a close-ended range.

The pH of the contacting step also is not particularly limited, so long as the first and second resins in the mixed mode resin composition are stable and can adequately function to separate the desired molecules. Generally, the pH will range from 3-13 and preferably, the method will operate at a near neutral pH (e.g., 6-8, about 7, or a physiological pH of about 7.4).

In step (c), the EVs in the sample are separated from the mixed mode resin composition to obtain a sample containing EVs at a higher concentration than prior to step (b). A suitable eluent is used to separate the EVs from the sample. Typical eluents include buffered aqueous solutions, for example, a sodium dodecyl sulfate (SDS) aqueous solution and an EDTA aqueous solution.

Removing residual unbound fluorophore and other unbound molecules results in a sample containing labeled EVs that can be detected with increased sensitivity (e.g., an increased signal to noise ratio) for use in any desired downstream cytometric, imaging, or other detection processes. These downstream processes include, e.g., proteomic analysis, cytometric studies, and nanoparticle analysis.

In some embodiments, the inventive method includes using nanoparticle analysis to analyze the sample containing extracellular vesicles. Nanoparticle analysis includes flow cytometry, imaging cytometry, fluorescence microscopy, nanoparticle tracking analysis (e.g., via NanoSight LM10 instrument, Malvern Instruments Ltd., Malvern, UK, and ZETAVIEW™ instrument, Particle Metrix, GmbH, Ammersee, Germany), single particle interferometric reflectance imaging sensing (SP-IRIS, e.g., via exoview technology available from NanoView Biosciences, Boston, MA), tunable resistance pulse sensing (TRPS, available from Izon Science, Ltd.), surface-plasmon-resonance (SPR) platform technologies (e.g., nano-plasmonic exosome (nPLEX) for high-throughput exosome protein profiling by optical transmission through periodic nanoholes), mass cytometry, and electron microscopy (e.g., removing gold-labeled antibodies).

In some embodiments, the inventive method includes using proteomic assays to analyze the sample containing extracellular vesicles. Proteomic assays include microBCA assay (Thermo Scientific., Northumberland, UK) and spectrophotometry assays (e.g., NanoDrop™, available from Thermo Scientific), gel electrophoresis, peptide mass fingerprinting, mass spectrometry, and sequencing.

The invention further provides a method of labeling an EV comprising
  (a) contacting an EV and a fluorophore that labels proteins to provide a mixture comprising a labeled EV and unbound fluorophore;
  (b) removing the unbound fluorophore by contacting the mixture with a mixed mode resin composition comprising a first resin and a second resin, wherein
  the first resin removes the unbound fluorophore and any other unbound molecules by a size exclusion mechanism; and
  the second resin transiently and reversibly binds to the EV in a calcium-dependent manner;
  (c) first eluting any unbound molecules; and
  (d) second eluting in the presence of at least one additive that selectively elutes the EV.

Step (a) of the labeling method is directed to contacting an EV and a fluorophore that labels proteins to provide an EV that is bound to the fluorophore. The fluorophore typically is any moiety that absorbs light, has a maximum emission wavelength in a range of about 380-780 nm (particularly between 400-700 nm), and that can bind to a protein found on the EV. The fluorophore typically will include at least one functional group that can form a chemical bond with a functional group on the protein (e.g., —NH$_2$, —COOH, or —SH group). The functional group on the fluorophore can be, for example, a sulfur-containing moiety (e.g., thio), an amino group, a hydroxyl group, a halo group, a carboxyl group, aryl, heteroaryl, or heterocyclyl prior to reaction with the protein. Specific functional groups on the fluorophore include isothiocyano, cyano, thio, succinimidyl ester, maleimido, aminomaleimido, hydrazido, amino, hydroxyl, carboxyl, or chloro. The fluorophore can be, for example, a xanthene dye, which includes a fluorescein, an eosin, and a rhodamine, a coumarin, a cyanine, a phycoerythrin, or a combination thereof.

Specific examples of a fluorescein include fluorescein isothiocyanate (FITC), fluorescein amidite, 6-carboxyfluorescein (6-FAM), carboxyfluorescein diacetate succcinimidyl ester (CFDA-SE), carboxyfluorescein succinimidyl ester (CFSE), fluorescein isothiocyanate (FITC), rose bengal, methylene blue, merbromin, Oregon Green, Tokyo Green, SNAFL, carboxynaphthofluorescein, ALEXA FLUOR™ 488, FLUOPROBES™ 488, and DYLIGHT™ 488.

Specific examples of an eosin include Eosin Y and Eosin B.

Specific examples of a rhodamine include Rhodamine 6G, Rhodamine B, carboxytetramethylrhodamine (TAMRA), tetramethylrhodamine (TMR) and its isothiocyanate derivative (TRITC) and, sulforhodamine 101, Rhodamine Red, ALEXA FLUOR™ dyes (e.g., ALEXA FLUOR™ 546, ALEXA FLUOR™ 555, ALEXA FLUOR™ 633; ThermoFisher Scientific, Waltham, MA), DYLIGHT™ fluor dyes (e.g., DYLIGHT™ 550, DYLIGHT™ 633, and HILYTE™ fluor dyes (HILYTE™ fluor 555, HILYTE™ 594).

Other specific examples of a xanthene include 9H-xanthene and 10H-9-oxaanthracene.

Specific examples of a coumarin include 3-(2-benzothiazolyl)-7-(diethylamino)coumarin, 3-(2-benzimidazolyl)-7-(diethylamino)coumarin, Coumarin 545T, Coumarin 102, Coumarin 314, Coumarin 6H, 7-(diethylamino)-3-(1-methyl-2-benzimidazolyl)coumarin, Coumarin 153, Coumarin 478, Coumarin 498, Coumarin 504T, Coumarin 521T, Coumarin 525, Coumarin 337, Coumarin 510, 3,3'-carbonylbis(7-diethylaminocourmarin), coumarin-3-carboxylic acid, 7-(diethylamino)coumarin, 7-(dimethylamino)-4-methylcoumarin, 7-(dimethylamino)-4-(trifluoromethyl)coumarin, 7-(diethylamino)coumarin-3-carboxylic acid, 7-(diethylamino)coumarin-3-carbonitrile, 7-(diethylamino)-4-(trifluoromethyl)coumarin, 7-(diethylamino)-4-(hydroxymethyl)coumarin, 7-(diethylamino)-3-(2-thienyl)coumarin, 7-(diethylamino)-3-phenylcoumarin, ethyl 7-(diethylamino)coumarin-3-carboxylate, ethyl 6-[4-(diphenylamino)phenyl]coumarin-3-carboxylate, 7-(ethylamino)-4-methylcoumarin, 7-(ethylamino)-4,6-dimethylcoumarin, hexyl 7-(diethylamino)coumarin-3-carboxylate, 7-diethylamino-4-methylcoumarin, 4-methyl-7-morpholino-8-azacoumarin, and Solvent Red 197.

Specific examples of a cyanine include sulfonated cyanines (sulfo-Cy3, sulfo-Cy5, sulfoC7) and non-sulfonated cyanines (Cy2, Cy3, Cy3.5, Cy5, Cy5.5, Cy7, Cy7.5, and allphycocyanin (APC)).

Specific examples of a phycoerythrin include R-phycoerythrin (R-PE), B-phycoerythrin (B-PE), and phycoerythrin 545 (PE545).

In some preferred instances, the fluorophore is 6-carboxyfluorescein (6-FAM), carboxyfluorescein diacetate succcinimidyl ester (CFDA-SE), carboxyfluorescein succinimidyl ester (CFSE), or fluorescein isothiocyanate (FITC). More preferably, the fluorophore is carboxyfluorescein succinimidyl ester (CFSE).

Step (b) of the labeling method is directed to removing any unbound fluorophore that remains in the sample and any other unbound molecule that may be present by contacting the mixture with a mixed mode resin composition comprising a first resin and a second resin. The first resin, second resin, including the calcium-dependent phospholipid ligand (e.g., a TIM-4 fusion protein or annexin V), and contacting step are as described herein.

In step (c) of the labeling method, unbound molecules (e.g., unbound fluorophore, protein, polypeptide, peptide, lipoprotein, nucleic acid, synthetic label, and/or metal) can be first eluted from the mixture, typically in the presence of calcium. Once unbound molecules are removed from the mixture, step (d) is directed to a second eluting step in the presence of at least one additive (e.g., a chelating agent and/or salt) that releases the EV from the second resin and selectively elutes the labeled EV. Step (d) allows for fluorolabeled EVs to be further isolated from molecules (e.g., proteins) that are trapped by the first resin by at least a size exclusion mechanism. The eluents and additives (e.g., chelating agent and/or salt) are as described herein.

A benefit of the inventive methods is the ability to perform such methods using a robotic (i.e., automated) high-throughput system. Typically, such system will require the use of at least one multi-well filter plate (e.g., a 96-well plate or 384-well plate) that can have a pore size that is suitable depending on the size of the mixed mode resin composition (i.e., first and second resins). The samples can be eluted through the filter plates using either gravity or centrifugation.

In any of the methods described herein, about 70% (about 75%, about 78%, about 80%, about 82%, about 85%, about 88%, about 90%, about 92%, about 94%, about 95%, about 96%, about 97%, about 98%, or about 99%) or more of the unbound molecules, including unbound fluorophore, are removed from the sample that contains EVs. The removal of unbound molecules provides a sample that contains EVs at a higher concentration than prior to the inventive method.

In some embodiments, the purity of the purified EVs is about 85% or greater (e.g., about 86% or greater, about 88% or greater, about 90% or greater, about 92% or greater, about 94% or greater, about 96% or greater, about 98% or greater, about 99% or greater, or about 99.5% or greater). Preferably, the purity of the purified EVs is about 95% or greater or about 97% or greater.

In some embodiments, the inventive method includes proteomic analysis of the extracellular vesicle. Proteomic analysis involves investigating the proteins associated with the extracellular vesicle.

In some embodiments, the proteomic analysis involves gel electrophoresis of the extracellular vesicle to separate and visualize the associated proteins. In some embodiments, the gel electrophoresis involves denaturing proteins in the presence of a detergent such as sodium dodecyl sulfate (SDS). In some embodiments, the gel electrophoresis involves use of a polyacrylamide gel. In some embodiments, the gel electrophoresis involves silver stain, Coomassie Brilliant Blue dye, or zinc. In some embodiments, the gel electrophoresis involves Stain-Free gel which use trihalocompounds that covalently bind to tryptophan, an amino acid found in most protein samples, to fluoresce under ultraviolent (UV) light (e.g., systems available through Bio-Rad Laboratories, Inc).

In some embodiments, the proteomic analysis involves peptide mass fingerprinting. In some embodiments, the proteomic analysis involves mass spectrometry. In some embodiments, the proteomic analysis involves sequencing. In some embodiments, the sequencing involves RNA sequencing (RNAseq) to analyze the sample containing extracellular vesicles. In some embodiments, the sequencing involves DNA sequencing (DNAseq) to analyze the sample containing extracellular vesicles.

Alternatively or in addition, proteins, such as RNA or DNA, are sequenced from the eluted unbound molecules (i.e., not the EVs).

Another benefit of the inventive methods is that use of a fluorophore that labels proteins, such as CFSE, prior to use with Stain-Free gels results in a 10-100-fold increase in sensitivity over gels using Coomassie Brilliant Blue and the standard Stain-Free method. This allows for proteins to be detected and retrieved using the Stain-Free method that otherwise would not have been detected and retrieved for analysis.

Another benefit of the inventive methods as is that use of a fluorophore that labels proteins, such as CFSE, prior to use with Stain-Free gels allows for downstream analysis methods such as western blotting and mass spectrometry. Silver staining, while very sensitive, is not compatible with western blotting and mass spectrometry. Further, silver staining requires a long staining protocol and the results are easily affected by a number of factors such as reagent quality, incubation times, and gel thickness.

The following embodiments further illustrate the invention but, of course, should not be construed as in any way limiting its scope.

1. A method of purifying extracellular vesicles in a sample comprising extracellular vesicles and molecules that are not bound to the extracellular vesicles, the method comprising:
    (a) providing a mixed mode resin composition comprising
        a first resin having pores with a pore size that traps unbound molecules having a size less than or equal to 1,000,000 Da in its pores by at least by a size exclusion mechanism, and
        a second resin comprising at least one affinity ligand;
    (b) contacting the sample with the mixed mode resin composition for a time sufficient to trap at least a portion of the unbound molecules having a size less than or equal to 1,000,000 Da in the first resin from the sample; and
    (c) separating the sample from the mixed mode resin composition after the contacting in (b) and obtaining a sample containing extracellular vesicles at a higher concentration than prior to step (b).

2. The method of embodiment 1, wherein the first resin comprises at least one affinity ligand to bind the molecules trapped in the pores.

3. The method of embodiment 1 or embodiment 2, wherein the second resin binds at least a portion of the unbound molecules.

4. The method of embodiment 1 or embodiment 2, wherein the second resin transiently binds to a phospholipid membrane in the extracellular vesicle in a calcium-dependent manner.

5. The method of embodiment 4, wherein after (b), the method further comprises
    (b-2) first eluting any molecule not bound to the first and second resins; and
    (b-3) second eluting in the presence of at least one additive, wherein the second eluting selectively elutes the extracellular vesicles.

6. A method of labeling an extracellular vesicle comprising
    (a) contacting an extracellular vesicle and a fluorophore that labels proteins to provide a mixture comprising a labeled extracellular vesicle and unbound fluorophore;
    (b) removing the unbound fluorophore by contacting the mixture with a mixed mode resin composition comprising a first resin and a second resin, wherein
        the first resin removes the unbound fluorophore and any other unbound molecules by a size exclusion mechanism; and
        the second resin transiently and reversibly binds to the extracellular vesicle in a calcium-dependent manner;
    (c) first eluting any unbound molecules; and
    (d) second eluting in the presence of at least one additive that selectively elutes the extracellular vesicle.

7. The method of embodiment 6, wherein the fluorophore is a xanthene, a fluorescein, an eosin, a rhodamine, a coumarin, a cyanine, a phycoerythrin, or a combination thereof.

8. The method of embodiment 6, wherein the fluorophore is 6-carboxyfluorescein (6-FAM), carboxyfluorescein diacetate succcinimidyl ester (CFDA-SE), carboxyfluorescein succinimidyl ester (CFSE), or fluorescein isothiocyanate (FITC).

9. The method of any one of embodiments 1-8, wherein the first resin comprises a first bead comprising (i) a porous core comprising a matrix material and at least one affinity ligand, (ii) a porous shell, and (iii) optionally at least one second affinity ligand coated on the exterior surface of the bead.

10. The method of any one of embodiments 1-3, wherein the second resin comprises a second bead comprising a matrix material and at least one ligand coated on the exterior surface of the bead that has an affinity for at least one unbound molecule in the sample.

11. The method of any one of embodiments 4-9, wherein the second resin comprises a second bead comprising a matrix material and the surface of the bead is conjugated to at least one ligand with an affinity for the extracellular vesicle.

12. The method of embodiment 11, wherein the ligand with an affinity for the extracellular vesicle is at least one calcium-dependent phospholipid ligand.

13. The method of embodiment 12, wherein the at least one calcium-dependent phospholipid ligand comprises a phosphatidylserine receptor.

14. The method of embodiment 13, wherein the phosphatidylserine receptor is a transmembrane immunoglobulin and mucin domain (TIM) protein or annexin V.

15. The method of any one of embodiments 5-9 and 11-14, wherein the additive that selectively elutes the purified extracellular vesicle is a calcium chelator.

16. The method of embodiment 15, wherein the calcium chelator is selected from the group consisting of ethylenediaminetetraacetic acid (EDTA), ethylenediamine-N,N'-disuccinic acid (EDDS), ethylene glycol-bis(β-aminoethyl ether)-N,N,N',N'-tetraacetic acid (EGTA), Fura-2, (1,2-bis(o-aminophenoxy)ethane-N,N,N',N'-tetraacetic acid) (BAPTA), 5,5'-dibromo-BAPTA, 5,5'-difluoro-BAPTA, 5,5'-dimethyl-BAPTA, 5-methyl-5'-nitro-BAPTA, 5-nitro-BAPTA, 4-trifluoromethyl-BAPTA, ethylenediamine, diethylenetriamine, catechol, cryptand, dimethylglyoxime, glutamic acid, gluconic acid, and a combination thereof.

17. The method of embodiment 11, wherein the ligand with an affinity for the extracellular vesicle binds to a heparin-binding molecule on the surface of the extracellular vesicle.

18. The method of embodiment 17, wherein the ligand with an affinity for the extracellular vesicle is heparin.

19. The method of any one of embodiments 5-9, 17, and 18, wherein the additive that selectively elutes the purified extracellular vesicle is a salt.

20. The method of any one of embodiments 5-9 and 11-19, wherein the first eluting in step (c) takes place in the presence of calcium.

21. The method of any one of embodiments 9-20, wherein the matrix material and/or porous shell comprises a synthetic or natural polymer.

22. The method of embodiment 21, wherein the synthetic or natural polymer is selected from a polystyrene, a polyalkylene, a polyester, polydivinylbenzene, an acrylamide polymer, a polyacrylate, a vinyl ester polymer, a vinylamide polymer, agarose, agarobiose, agar, cellulose, dextran, chitosan, konjac, carrageenan, gellan, alginate, and a combination thereof.

23. The method of embodiment 22, wherein the matrix material of the first bead is agarose.

24. The method of any one of embodiments 21-23, wherein the porous shell is the same material as the first matrix material.

25. The method of any one of embodiments 21-24, wherein the matrix material of the second bead is polystyrene, polyethylene, polypropylene, polyester, polydivinylbenzene, polyacrylamide, poly(meth)acrylate, polyethyl acrylate, polymethyl methacrylate, poly(hydroxyethyl) methacrylate, polyvinyl ester, poly(N-vinylacetamide), or a combination thereof.

26. The method of any one of embodiments 2 and 9-25, wherein the affinity ligand that binds the molecules trapped in the pores on the first resin is an amine, a quaternary ammonium compound, or a combination thereof.

27. The method of embodiment 26, wherein the affinity ligand is a trialkylamine or a tetraalkylammonium compound.

28. The method of embodiment 26 or embodiment 27, wherein the affinity ligand is trihexylamine, trioctylamine, tridecylamine, tridodecylamine, tri-octyl/decyl amine, N-dodecenyl-trialkylmethylamine, N-benzyl-N-methyl ethanolamine, a trilauryl monomethyl ammonium salt, N-methyl-N,N,N-trioctylammonium chloride, or a combination thereof.

29. The method of embodiment 9 or embodiment 10, wherein the second affinity ligand on the first bead or the affinity ligand on the second bead is an immunoglobulin, a biotinylated compound, or a combination thereof.

30. The method of any one of embodiments 9-29, wherein the second affinity ligand on the first bead or the affinity ligand on the second bead is an antibody, an antigen, streptavidin, biotin, avidin biotin, heparin, glutathione, protein A, protein G, protein A/G, an amino acid, a nucleotide, a carbohydrate, a lectin, a dye, a chelate, or a combination thereof.

31. The method of any one of embodiments 1-3 and 9-30, wherein the first resin traps unbound molecules having a size less than or equal to 1000 kDa by size exclusion, and the second resin binds unbound molecules having a size greater than 1000 kDa through affinity.

32. The method of embodiment 31, wherein the first resin traps unbound molecules having a size less than or equal to 900 kDa by size exclusion, and the second resin binds unbound molecules having a size greater than 900 kDa through affinity.

33. The method of embodiment 32, wherein the first resin traps unbound molecules having a size less than or equal to 700 kDa by size exclusion, and the second resin binds unbound molecules having a size greater than 700 kDa through affinity.

34. The method of any one of embodiments 1-33, wherein the unbound molecules comprise at least one protein, polypeptide, peptide, lipoprotein, nucleic acid, synthetic label, metal, or a combination thereof.

35. The method of embodiment 34, wherein the protein is a protein present in a biofluid selected from plasma, serum, urine, cerebrospinal fluid, saliva, tears, ascites, pleural effusion, and a combination thereof.

36. The method of embodiment 34, wherein the protein comprises a tissue culture protein.

37. The method of any one of embodiments 34-36, wherein the protein is an antibody, apolipoprotein A (ApoA), apolipoprotein B (ApoB), apolipoprotein E (ApoE), immunoglobulin G (IgG), immunoglobulin M (IgM), immunoglobulin A (IgA), immunoglobulin E (IgE), immunoglobulin D (IgD), albumin, globulin, factor IX, Tamm-Horsfall protein, transferrin, haptoglobin, prothrombin, alpha 1 acid glycoprotein, alpha 1 fetoprotein, cystatin C, ceruloplasmin, or a combination thereof.

38. The method of any one of embodiments 1-37, wherein about 70% or more of the unbound molecules and/or unbound fluorophore are removed from the sample.

39. The method of embodiment 38, wherein about 85% or more of the unbound molecules and/or unbound fluorophore are removed from the sample.

40. The method of embodiment 39, wherein about 95% or more of the unbound molecules and/or unbound fluorophore are removed from the sample.

41. The method of any one of embodiments 1-40, wherein the method is performed with a high-throughput filtering system.

42. The method of any one of embodiments 1-5, further comprising
(e) utilizing nanoparticle analysis to analyze the sample containing extracellular vesicles.

43. The method of any one of embodiments 1-5, further comprising
(e) utilizing proteomic assays to analyze the sample containing extracellular vesicles.

The following examples further illustrate the invention but, of course, should not be construed as in any way limiting its scope.

EXAMPLE 1

This example demonstrates a method of purifying EVs using a mixed mode resin composition in an embodiment of the invention.

Incubation tubes are loaded with (i) a sample containing EVs and unbound molecules and (ii) a mixed mode resin composition. The samples are then incubated for a suitable period of time (e.g., 0.5-4 hours). The tubes are spun in a centrifuge to concentrate the EVs. The supernatant is removed, and the purified EVs are collected. See FIG. 1.

EXAMPLE 2

This example demonstrates a method of purifying EVs using a resin in an embodiment of the invention.

A 500 mL bottle of resin suspended in 20% ethanol was shaken vigorously before 500 µL was transferred to a 1.5 mL Eppendorf tube. 100 µL of resin was then transferred from the 1.5 mL Eppendorf to each well of a 350 µL, 0.45 µm SUPOR™ Membrane, ACROPREP™ Advance 96-Well Filter Plate (Pall Corporation, New York, NY), ensuring the resin was continuously mixed before transfer. The 96-well filter plate was placed on top of a 96-well, 350 µL round bottom collection plate. Next, wells were filled with Dulbecco's phosphate-buffered saline (DPBS) and centrifuged at 100×g for 2 mins. Wells were immediately refilled with DPBS and centrifuged again for 100×g for 2 mins. Wells were then immediately refilled with 50 µL DPBS. 150 µL of the medium being purified was then layered on top of the resin. A large pipette was used to mix the sample in each well.

Bovine serum albumin (BSA) concentrations were calculated using a NANODROP™ 2000 Spectrometer (Thermo Fisher Scientific, Waltham, MA). Prior to recording the concentration using the NANODROP™, its sensor was rinsed with deionized water before a baseline reading was taken using DPBS. 2 µL of sample was then placed on the sensor and a concentration reading was recorded three times. Recordings were exported to .xml files.

Particle concentration and diameter distribution were characterized by nanoparticle tracking analysis (NTA) with a NanoSight LM10 instrument (Malvern Instruments Ltd., Malvern, UK), equipped with a 405 nm LM12 module and electron multiplying charge-coupled device (EMCCD) camera (DL-658-OEM-630, Andor Technology, Belfast, Ireland). Video acquisition was performed with NTA software v3.2, using a camera level of 14. Three 30-second videos were captured per sample. Post-acquisition video analysis used the following settings: minimum track length=5, detection threshold=4, automatic blur size=2-pass, and maximum jump size=12.0.

PC3pip cells (cell line that expresses human PSMA) were cultured in T-175 flasks in 30 mL of phenol red-free RPMI 1640 medium with 1% L-glutamate, 1% penicillin streptomycin (Pen-Strep), 10% EV-free fetal bovine serum (FBS), and 0.1% beta-mercaptoethanol (β-ME). Supernatant was aspirated from 10 flasks and spun twice at 2000×g for 20 mins in 50 mL FALCON™ tubes (Fisher Scientific, Hampton, NH). Supernatant was aspirated from each of the tubes, leaving 5 mL at the bottom, and pooled before being added to a 60 mL 100 kDa JUMBOSEP™ filter (Pall Laboratory, New York, NY), and centrifuged at 2000×g for 15-20 mins until 5 mL remained. Further supernatant was added, and the process was repeated until all supernatant had been filtered. Filtered supernatant was then aliquoted into 1.5 mL low-protein binding Eppendorf tubes and stored at 4° C.

Unstained $2.5 \times 10^{11}$ PC3pip EVs, counted using NTA, were added to 10 mM carboxyfluorescein succinimidyl ester (CFSE) and incubated at 37° C. for 2 hours before being aliquoted onto a NAP™-5 size-exclusion chromatography column (GE Healthcare, Chicago, IL), with fractions 3 and 4 being collected. Fractions 3 and 4 were then enumerated using NTA. Unstained $2.5 \times 10^{11}$ PC3pip EVs were also added to NAP™-5 size-exclusion chromatography column, with fractions 3 and 4 being collected and enumerated using NTA.

Figure 3:
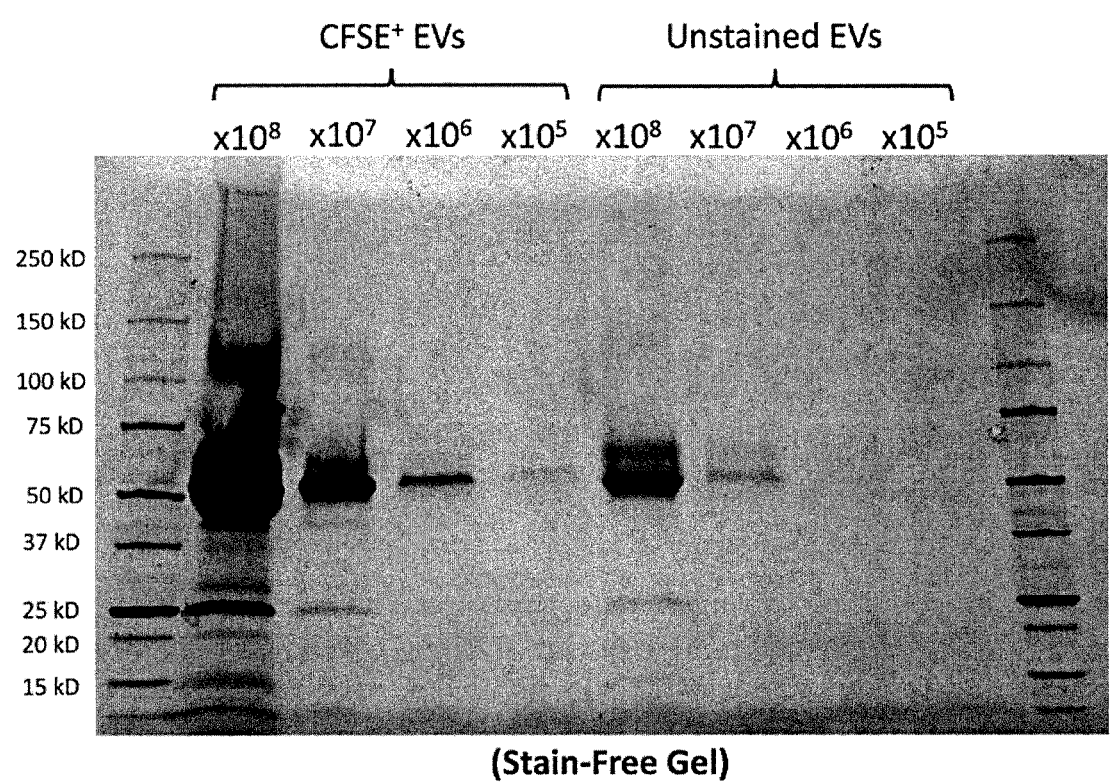

$1 \times 10^8$, $1 \times 10^7$, $1 \times 10^6$, $1 \times 10^5$ of unstained and CFSE-stained PC3pip EVs were made up to a volume of 30 μL using DPBS and an aliquot of NAP™-5 fraction 3+4 before 10 μL of 4× Laemmli buffer and 4 μL of 10% TRITON™ X-100. Samples were incubated at 95° C. for 10 minutes before being loaded onto a 10-well, 50 μL, 12% MINI-PROTEAN™ TGX STAIN-FREE™ Protein Gel (BioRad, Hercules, CA). Gels were run in tris(hdyroxymethyl)aminomethan (Tris)/Glycine SDS running buffer. See FIG. 3.

Flow cytometric analysis was carried out using a previously developed nanoFACS methodology (Morales-Kastresana et al., *Scientific Reports*, 7: 1878-1887(2017)). Briefly, an ASTRIOS™ EQ jet-in-air system (Beckman Coulter, Brea, CA), configured with 5 lasers (355, 405, 488, 561, and 640 nm wavelength), where Side Scatter (SSC) can be detected and used as a trigger at laser wavelength with the exception of the 355 nm laser. EV analyses were carried out using a 561-SSC trigger with the 561-SSC voltage and threshold settings adjusted to allow 10,000-13,000 events of background reference noise per second. Samples were loaded and run for 5 minutes until the event rate was stable, and then 500,000 acquisition events were saved. All samples were run at a 0.3 psi differential pressure, monitoring stability closely. Data was acquired using Summit v6 (Beckman Coulter) and analyzed with FLOWJO™ v10.1r5 software (TreeStar, Ashland, OR).

Exported .xml spreadsheets from the NANODROP™ (Thermo Fisher Scientific, Waltham, MA) software were compiled and plotted using scripts written in MATLAB™ v9.3.0 (The MathWorks Inc., Natick, MA).

Figure 4:
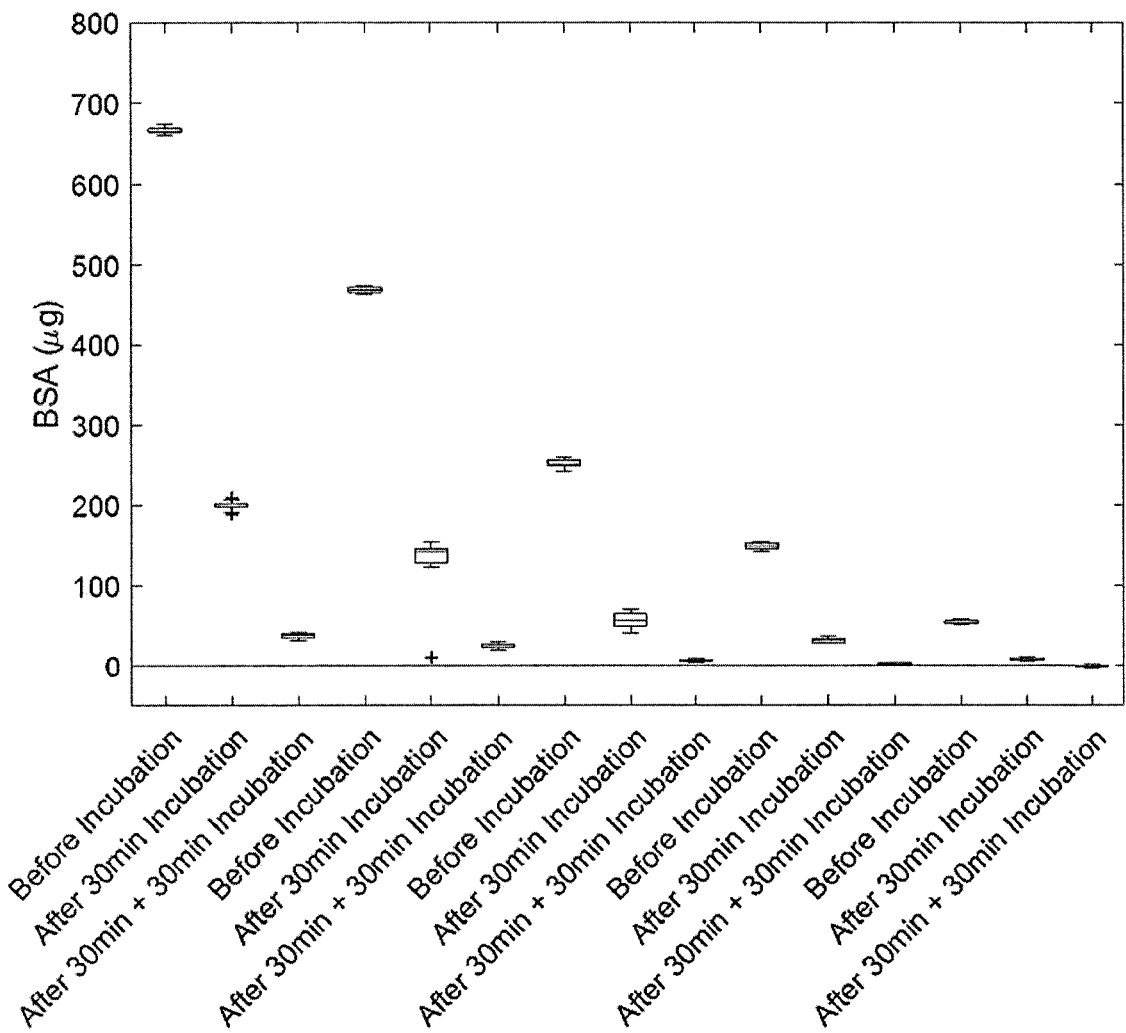

In order to test the binding capacity and incubation time of the resin, varying concentrations of bovine serum album (BSA) were incubated with 100 μL of resin for 30 minutes, which was followed by a second 30-minute incubation. It was observed that a single 30-minute incubation with 100 μL of resin is capable of removing up to 450 μg of BSA from the sample. After two sequential 30 min incubations, more than 90% of the BSA was removed. See FIG. 4.

EXAMPLE 3

This example demonstrates that a method of purifying EVs using a mixed mode resin in an embodiment of the invention allows for identification of an increased number of types of RNA compared to non-purified EVs.

Figure 7:
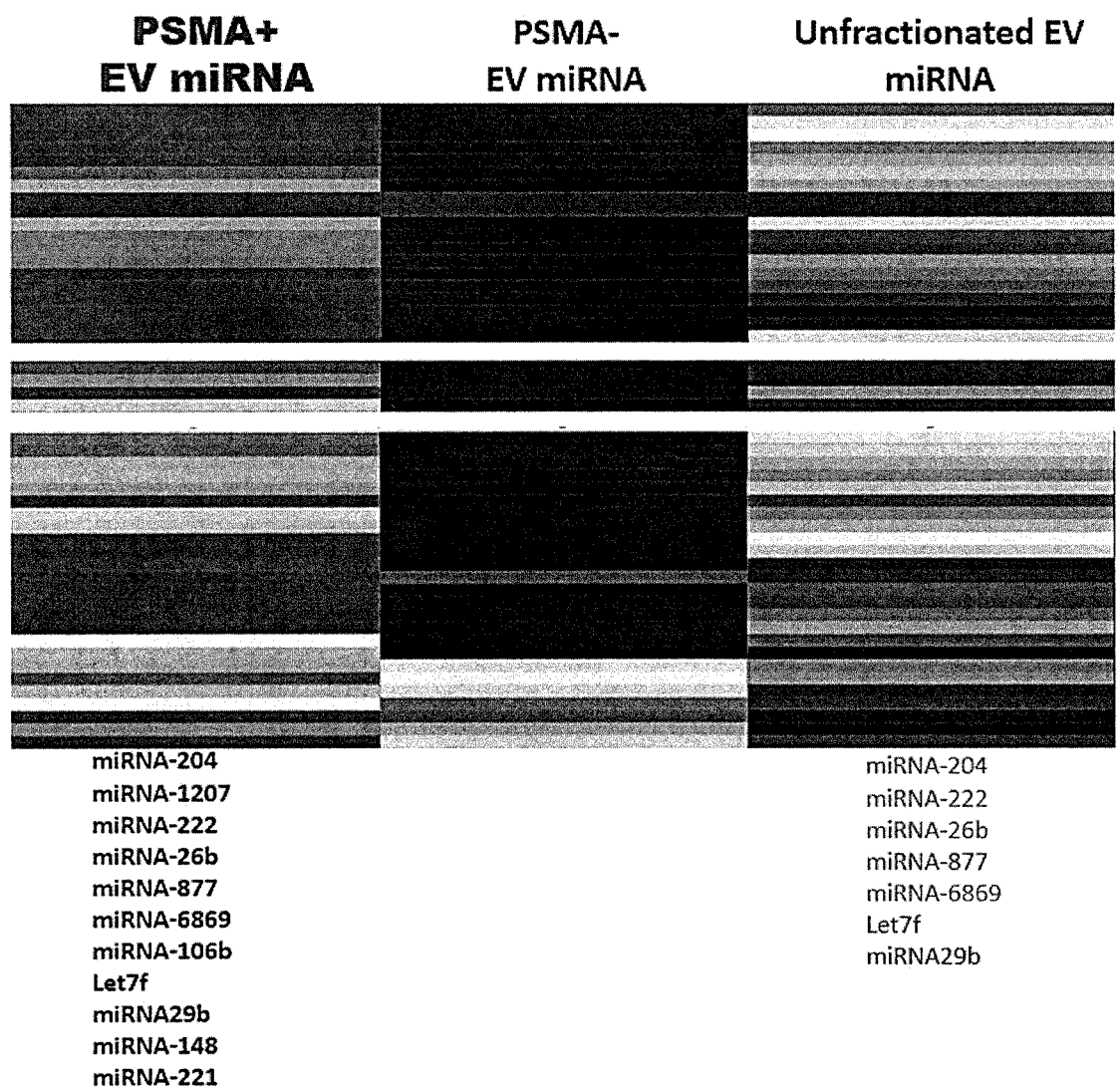
FIG. 7 is a diagram showing the types and relative amounts of miRNAs detected in accordance with an embodiment of the invention.

A portion of a sample was purified using prostate-specific membrane antigen (PSMA) and the PSMA positive, PSMA negative, and unfractionated EV samples were analyzed and sequenced (RNA seq). The sequencing revealed that the PSMA positive fraction contained at a detectable level the microRNAs miRNA-204, miRNA-1207, miRNA-222, miRNA-26b, miRNA-877, miRNA-6869, miRNA-106b, Let7f, miRNA29b, miRNA-148, and miRNA-221 (see FIG. 7, image is post-hierarchical clustering). The PSMA negative fraction did not reveal the presence of microRNAs and the unfractionated EV sample contained at a detectable level the microRNAs miRNA-204, miRNA-222, miRNA-26b, miRNA-877, miRNA-6869, Let7f, miRNA29b. Accordingly, the EV purification allowed for an increased sensitivity of the amount of each miRNA and importantly, the increased sensitivity allowed for detection of four additional miRNAs (i.e., miRNA-1207, miRNA-106b, miRNA-148, and miRNA-221).

Figure 5A:
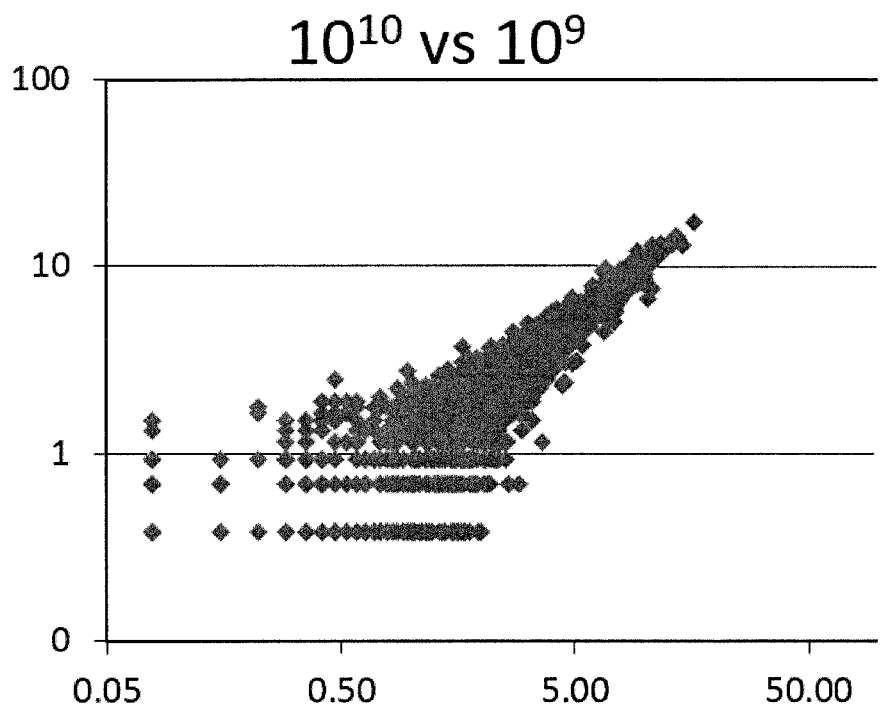
FIG. 5A is a correlation plot showing miRNAs detected with input of $10^9$ vs $10^{10}$ EVs.
Figure 5B:
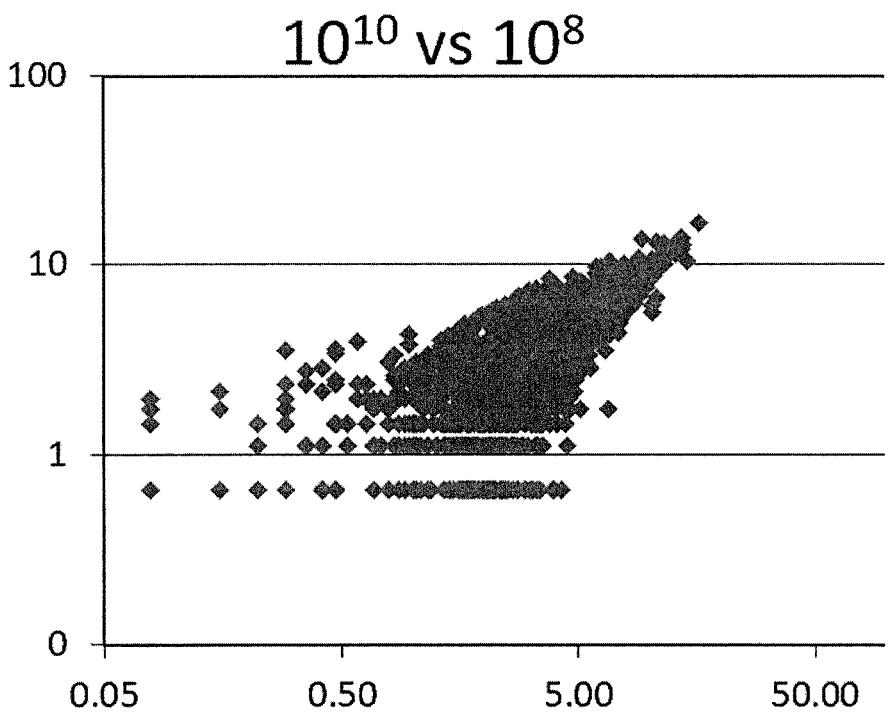
FIG. 5B is a correlation plot showing miRNAs detected with input of $10^8$ vs $10^{10}$ EVs.
Figure 5C:
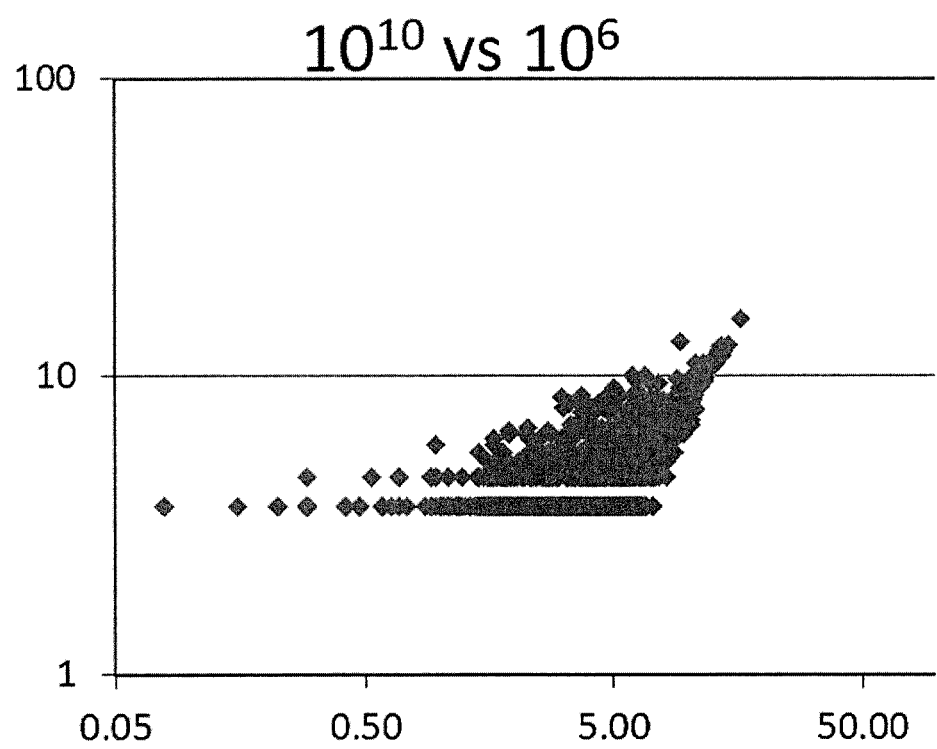
FIG. 5C is a correlation plot showing miRNAs detected with input of $10^6$ vs $10^{10}$ EVs.

FIG. 5A is a correlation plot showing miRNAs detected with input of $10^9$ vs $10^{10}$ EVs. FIG. 5A shows that a correlation exists between theses input levels, so fewer than one billion EVs are required as input for identification of miRNA signatures from EV subsets. FIG. 5B is a correlation plot showing miRNAs detected with input of $10^8$ vs $10^{10}$ EVs. FIG. 5B shows that a correlation exists between theses input levels, so fewer than one hundred million EVs are required as input for identification of miRNA signatures from EV subsets. FIG. 5C is a correlation plot showing miRNAs detected with input of $10^6$ vs $10^{10}$ EVs. FIG. 5C shows that a correlation exists between theses input levels, so fewer than one million EVs are required as input for identification of miRNA signatures from EV subsets.

EXAMPLE 4

This example demonstrates a method of purifying EVs and removing unbound labels using a mixed mode resin composition in an embodiment of the invention.

Spin tubes were loaded with (i) a sample containing EVs with labels and unbound molecules (including unbound labels) and (ii) a mixed mode resin composition. The samples were incubated for a suitable period of time (e.g., 0.5-4 hours). The tubes were spun in a centrifuge. After centrifugation, the resin was in the pellet and the sample was aspirated from the top of the tube. The unbound labels were efficiently removed from the EVs and downstream processing and characterization of EVs occurred. This method was also successfully used to remove antibodies from the EVs after staining.

EXAMPLE 5

This example demonstrates a method of purifying EVs and removing unbound labels using a mixed mode resin composition in another embodiment of the invention.

Filter plates with pore sizes (<12 μm) were loaded with (i) a sample containing EVs and unbound molecules (including unbound labels) and (ii) a mixed mode resin composition.

The samples were incubated for a suitable period of time (e.g., 0.5-4 hours). The pore size of the filter plates allowed the sample to flow through while unbound molecules remained in the resin on top of filter. The filter pores are an example of a suitable depleting resin. The EVs were efficiently purified and downstream processing and characterization of EVs occurred. This method was also successfully used to remove antibodies from the EVs after staining.

EXAMPLE 6

This example demonstrates a method of purifying EVs and removing unwanted lipoprotein, protein or other macromolecular complexes using a mixed mode resin composition in a further embodiment of the invention.

Spin tubes were loaded with (i) a sample containing EVs and unbound molecules (including lipoprotein, protein or other macromolecular complexes) and (ii) a mixed mode resin composition. The samples were incubated for a suitable period of time (e.g., 0.5-4 hours). The tubes were spun in a centrifuge. After centrifugation, the EVs were aspirated from the top of the spin tube. Centrifugation is an example of a suitable depleting resin. The EVs were efficiently purified and downstream processing and characterization of EVs occurred.

EXAMPLE 7

This example demonstrates a method of purifying EVs and removing unwanted lipoprotein, protein or other macromolecular complexes using a mixed mode resin composition in yet another embodiment of the invention.

Filter plates with pore sizes (<12 μm) were loaded with (i) a sample containing EVs and unbound molecules (including unwanted lipoprotein, protein or other macromolecular complexes) and (ii) a mixed mode resin composition. The samples were incubated for a suitable period of time (e.g., 0.5-4 hours). The pore size of the filter plates allowed the sample to flow through while the unwanted lipoprotein, protein or other macromolecular complexes remained in the resin on top of filter. The EVs were efficiently purified and downstream processing and characterization of EVs occurred.

EXAMPLE 8

This example demonstrates another method of purifying EVs and removing unwanted molecules using a mixed mode resin composition in an embodiment of the invention using selective capture.

Spin tubes were loaded with (i) a sample containing EVs and unbound molecules and (ii) a mixed mode resin composition. The samples were incubated for a suitable period of time (e.g., 0.5-4 hours). The tubes were spun in a centrifuge. After centrifugation the EVs were aspirated from the top of the spin tube. The EVs were efficiently purified (from a mixture of EVs with labels in a complex heterogeneous sample, where some labels were bound and some were not) and downstream processing and characterization of EVs occurred.

EXAMPLE 9

This example demonstrates another method of purifying EVs and removing unwanted molecules using a mixed mode resin composition in an embodiment of the invention using selective capture.

Filter plates with pore sizes (<12 um) were loaded with (i) a sample containing EVs and unbound molecules (including) and (ii) a mixed mode resin composition. The samples were incubated for a suitable period of time (e.g., 0.5-4 hours). The pore size of the filter plates allowed the sample to flow through while the unwanted lipoprotein, protein or other macromolecular complexes remained in the resin on top of filter. The EVs were efficiently purified (from a mixture of EVs with labels in a complex heterogeneous sample, where some labels were bound and some were not) and downstream processing and characterization of EVs occurred. This method was also used to select for other macromolecular complexes.

EXAMPLE 10

This example demonstrates another method of purifying EVs and removing unwanted molecules using a mixed mode resin composition in an embodiment of the invention using selective capture.

Filter plates with pore sizes (<10 um) were loaded with (i) a sample containing EVs and unbound molecules, (ii) a mixed mode resin composition, (iii) selective capture beads, and (iv) general capture beads. The samples were incubated for a suitable period of time (e.g., 0.5-4 hours). The pore size allowed the smaller selective capture beads to flow through while preventing flow through of large general capture beads (>12 um). The subset of EVs were efficiently purified (from a mixture of EVs with labels in a complex heterogeneous sample) and downstream processing and characterization of subset of EVs occurred. This method was also used to select for other macromolecular complexes.

EXAMPLE 11

This example demonstrates the use of another method of removing unbound molecules using a mixed mode resin.

A cytometric chamber, including one area for cytometric visualization and a second area with mixed mode resin, wherein the two areas are separated by a filter with <10 um pore size, were used to remove unbound labels from the sample visualization area of the chamber, thereby reducing background levels and improving assay sensitivity in downstream processing.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of purifying extracellular vesicles in a sample comprising extracellular vesicles and molecules that are not bound to the extracellular vesicles, the method comprising:
   (a) providing a mixed mode resin composition comprising
      a first resin having pores with a pore size that traps unbound molecules having a size less than or equal to 1,000,000 Da in its pores by at least by a size exclusion mechanism, wherein the first resin comprises at least one affinity ligand to bind one or more of the molecules trapped in the pores, and wherein the at least one affinity ligand present in the first resin is a quaternary ammonium compound or a trialkylamine; and
      a second resin which comprises a bead comprising a non-porous matrix material made of a synthetic polymer and an outer surface, wherein the outer surface is coated with at least one affinity ligand;
   (b) contacting the sample with the mixed mode resin composition for a time sufficient to trap at least a portion of the unbound molecules having a size less than or equal to 1,000,000 Da in the first resin from the sample; and
   (c) separating the sample from the mixed mode resin composition after the contacting in (b) and obtaining a sample containing extracellular vesicles at a higher concentration than prior to step (b).

2. The method of claim 1, wherein the second resin binds at least a portion of the unbound molecules.

3. The method of claim 1, wherein the second resin transiently binds to a phospholipid membrane in the extracellular vesicle in a calcium-dependent manner.

4. The method of claim 3, wherein after (b), the method further comprises
   (b-2) first eluting any molecule not bound to the first and second resins; and
   (b-3) second eluting in the presence of at least one additive, wherein the second eluting selectively elutes the extracellular vesicles.

5. The method of claim 1, wherein the first resin comprises a first bead comprising (i) a porous core comprising a matrix material and the at least one affinity ligand, (ii) a porous shell, and (iii) optionally at least one second affinity ligand coated on the exterior surface of the first bead.

6. The method of claim 1, wherein the second resin comprises a second bead comprising a matrix material and at least one ligand coated on an exterior surface of the second bead that has an affinity for at least one unbound molecule in the sample.

7. The method of claim 1, wherein the second resin comprises a second bead, which is non-porous and which comprises a matrix material made of a synthetic polymer and an outer surface that is conjugated to at least one ligand with an affinity for the extracellular vesicle.

8. The method of claim 1, wherein the synthetic polymer is selected from the group consisting of a polystyrene, a polyalkylene, a polyester, polydivinylbenzene, an acrylamide polymer, a polyacrylate, a vinyl ester polymer, a vinylamide polymer, and a combination thereof.

9. The method of claim 1, wherein the method is performed with a high-throughput, cartridge, or multi-well filtering system.

10. The method of claim 1, further comprising
    (e) utilizing nanoparticle analysis, a nucleic acid assay, or a proteomic assay to analyze the characteristics or composition of the sample containing extracellular vesicles.

11. The method of claim 1, wherein the first resin comprises at least one affinity ligand to bind one or more of the molecules trapped in the pores, and wherein the at least one affinity ligand present in the first resin is a quaternary ammonium compound.

12. The method of claim 1, wherein the affinity ligand of the second resin is a calcium-dependent phospholipid ligand that comprises a phosphatidylserine receptor.

13. The method of claim 12, wherein the phosphatidylserine receptor is a transmembrane immunoglobulin or a mucin domain (TIM) protein.

14. The method of claim 1, wherein the affinity ligand of the second resin is heparin.

* * * * *